(12) United States Patent
Huang (10) Patent No.: US 6,673,052 B2
(45) Date of Patent: Jan. 6, 2004

(54) NONRETURN WARNING DEVICE FOR AN INTRAVENOUS DRIP INFUSION

(76) Inventor: Hai-Su Huang, 5F, No. 23, Fu-De S. Rd., San Zhong City, Taipei County (TW)

( * ) Notice: Subject to any disclaimer, the term of this patent is extended or adjusted under 35 U.S.C. 154(b) by 51 days.

(21) Appl. No.: 10/075,383

(22) Filed: Feb. 15, 2002

(65) Prior Publication Data

US 2003/0158526 A1 Aug. 21, 2003

(51) Int. Cl.$^7$ .............................. A61M 5/14; B67D 5/08
(52) U.S. Cl. ...................... 604/254; 604/251; 604/253; 222/67
(58) Field of Search ........................ 604/30, 246, 247, 604/251, 254, 256, 253, 255, 258; 137/192; 222/67

(56) References Cited

U.S. PATENT DOCUMENTS

| 3,931,818 | A | * | 1/1976 | Goldowsky | ............... | 604/254 |
| 4,340,050 | A | * | 7/1982 | Noiles | ............... | 604/246 |
| 6,419,662 | B1 | * | 7/2002 | Solazzo | ............... | 604/248 |

* cited by examiner

Primary Examiner—Michael J. Hayes
Assistant Examiner—Lina R Kontos
(74) Attorney, Agent, or Firm—Alan Kamrath; Rider Bennett, LLP (57) ABSTRACT

The present invention relates to a nonreturn warning device for an intravenous drip infusion which includes a top member and a bottom member both of which forms an accommodation which has an inlet pipe and an outlet pipe at the top and bottom thereof. The outlet pipe includes a flange around which a recess is provided. A conic valve with a middle hole is arranged onto the flange. A float with a cylindrical stopper is received in the accommodation formed after connection of the top member and the bottom member. The middle section of the float contains a magnetic element, and a warning device is fitted beside the top member. Besides, a magnetic reed switch is installed in the warning device. As the float sinks with the fluid surface in the accommodation, the magnetic element approaches the magnetic reed switch and the magnetic force of the float will activate a buzzer for giving out a warning sound which is transmitted through a headphone jack or a radio transmitter to the nurses' call station. Moreover, the cylindrical stopper is inserted through the middle hole of the conic valve when the float sinks with the fluid surface in the accommodation. And the outlet pipe can be sealed at the end of the intravenous drip in order for nurses to replace an I.V. container. Furthermore, the nonreturn warning device for an intravenous drip infusion is repeatedly usable.

7 Claims, 12 Drawing Sheets

NONRETURN WARNING DEVICE FOR AN INTRAVENOUS DRIP INFUSION

BACKGROUND OF THE INVENTION

1. Field of the Invention

The present invention relates to a nonreturn warning device for an intravenous drip infusion, and more particularly, to a device whose dripping tube is sealed to prevent air from entering into the blood vessel and, meanwhile, a warning device is activated after all the infusion solution has flow out. Therefore, the nurse can be reminded of a proper handling. Moreover, this nonreturn warning device is repeatedly usable.

2. Description of the Prior Art

It's common to administer an intravenous drip infusion for medication. When the intravenous drip is finished, the fluid pressure in the injection tube is suddenly lowered because the infusion solution is used up. Meanwhile, the fluid pressure of the blood is also reduced so that the blood comes back to the injection tube. Even, when the infusion solution is used up, the air in the injection tube will enter into the blood vessel of the patient, thereby causing medical troubles or even endangering the life of the patient. Hence, it's necessary to check the whole process during the intravenous drip infusion to and the above-mentioned, thereby occupying huge chunks of a nurse's working and leading to a great pressure.

Figure 1:
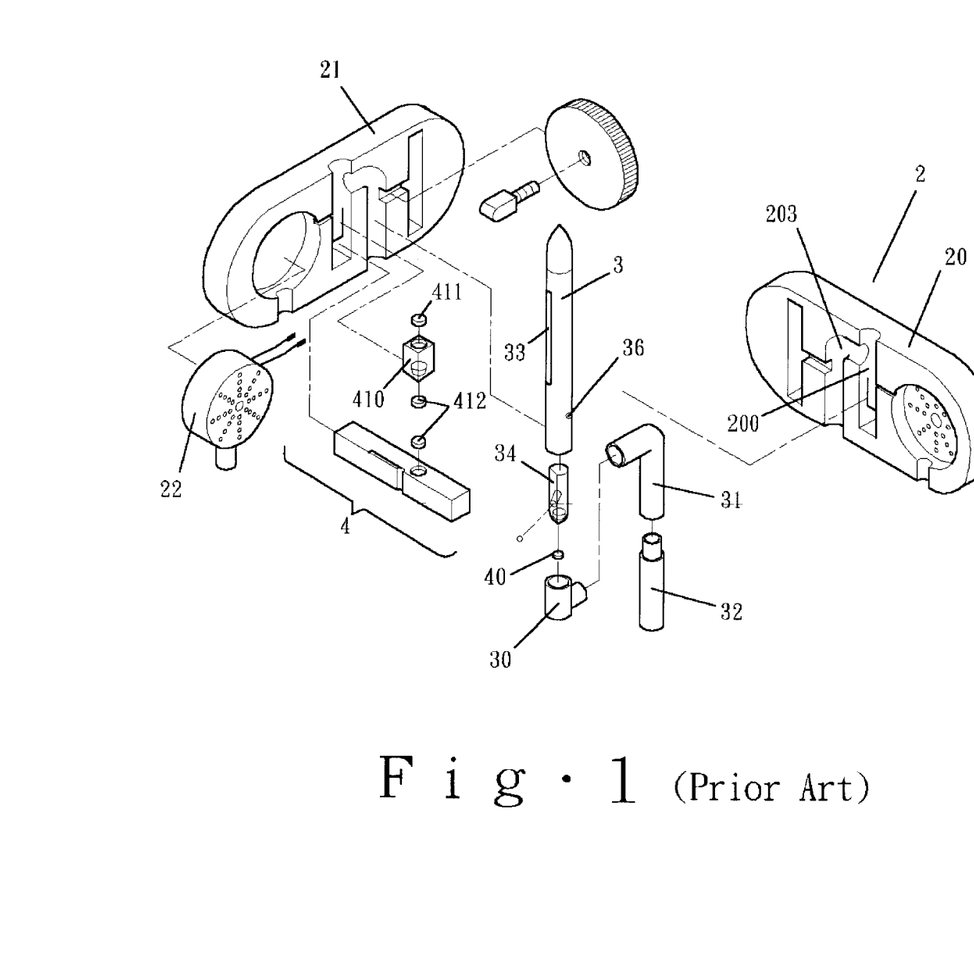
FIG. 1 is a perspective exploded view of a device for controlling intravenous drip infusion disclosed by Taiwan Utility Model No. 381494.

In addition to the costly electronic devices to monitor the rate and the duration of the intravenous drip, a few monitoring devices with more simple configuration have been disclosed. Taiwan Pat. No. 381494 (see FIGS. 1 through 3, corresponding to original FIGS. 2, 5, 6) describes a monitoring device which includes:

a main body 2 having a first half housing 20 and a second half housing 21, an longitudinal accommodation 200 in connection with an angle channel 203 extending to the bottom end of the main body 2, a conduit tee 30 and an elbow joint 31 being fitted to the connection position between the accommodation 200 and the angle channel 203, a buzzer 22 being provided at one side of the monitoring device while two leads of the buzzer 22 being connected to two indirect points at the bottom of the conduit tee 30;

a pointed bar 3 whose bottom end is secured to the conduit tee 30 and whose top end is inserted into the solution bottle, said pointed bar 3 having an outlet 36 arranged at the bottom thereof and corresponding to the side leg of the elbow joint 31 which is in connection with an solution tube 32, a number of longitudinal inlets 33 being provided on the pointed bar 3; and a magnetic induction assembly 4 having a float 34 floatable with the liquid surface and fitted to the inside of the pointed bar 3, a first magnet 40 fixed at the bottom of the float 34 and second magnets 411, 412 which are arranged in the accommodation 200 and move a movable piece 410 upward and downward.

When the float 34 is lowered to a certain level, the first magnet 40 will attract the second magnet 411 upwards to the bottom of the conduit tee 30. Meanwhile, an electric connection is created between both contact points through the conductivity of the second magnet 411; therefore, the buzzer 32 is automatically activated to give out a warning sound. However, the above-mentioned configuration is not only precise but also complicated and its production cost is high so that the product is not competitive. Moreover, the small float 34 and the magnets 40, 411, 412 don't react sensitively because of the insufficiency of the buoyancy and the magnetic force. In addition, this device can't be reused after sterilization so that the disposable feature will increase the cost burden of the users.

Figure 4:
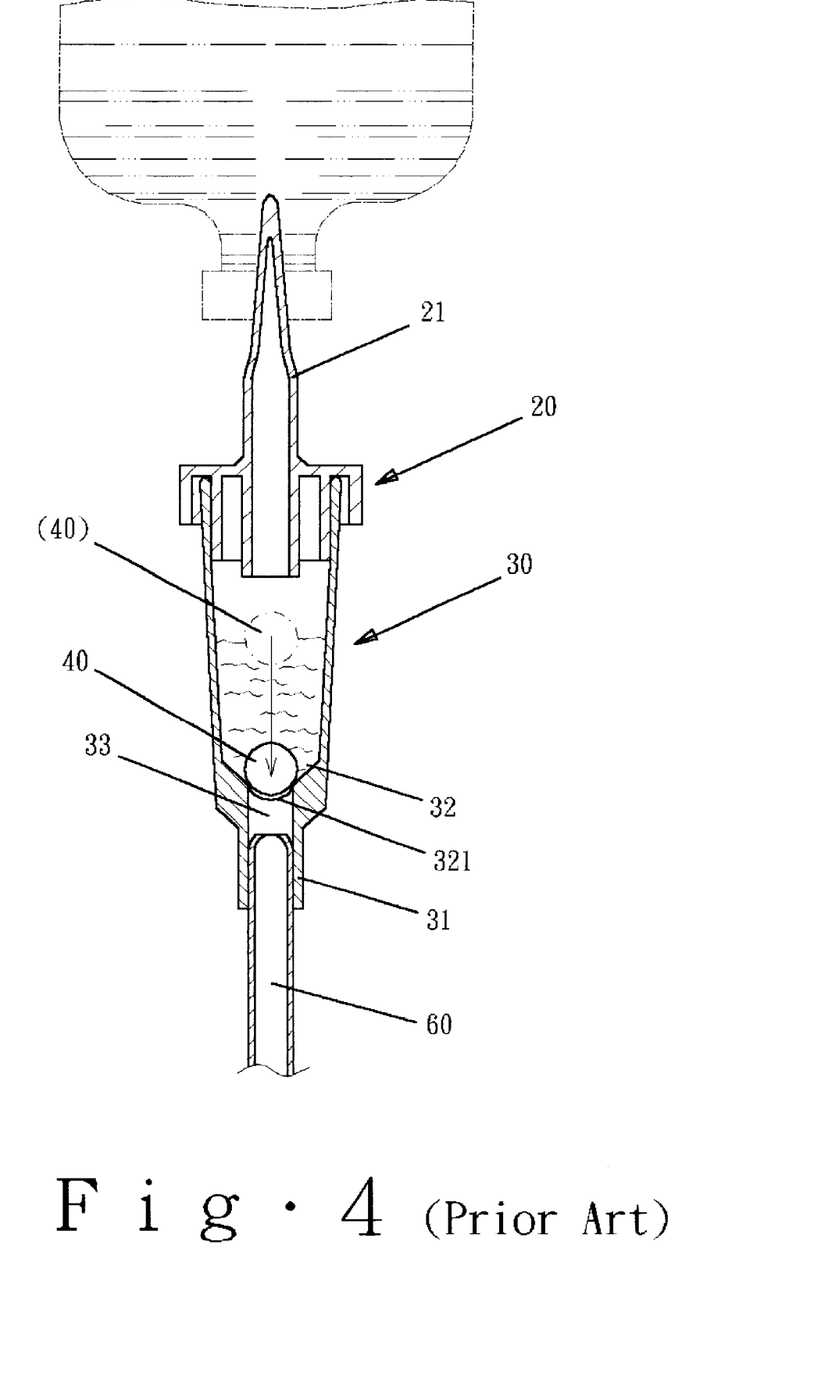
FIG. 4 is a sectional view of a device for controlling intravenous drip infusion disclosed by Taiwan Utility Model No. 394026.
Figure 5:
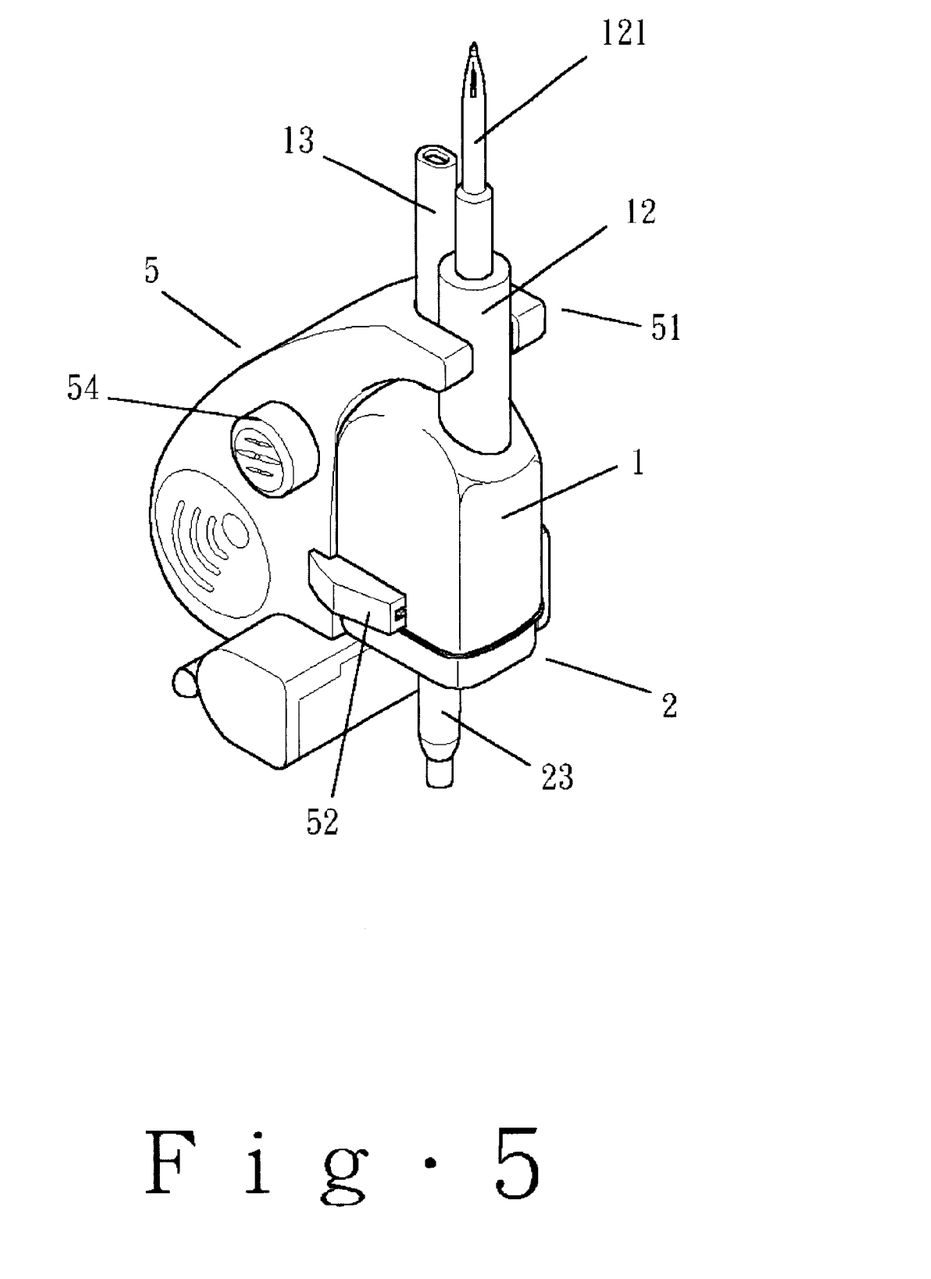
FIG. 5 is a perspective view of the present invention.
Figure 6:
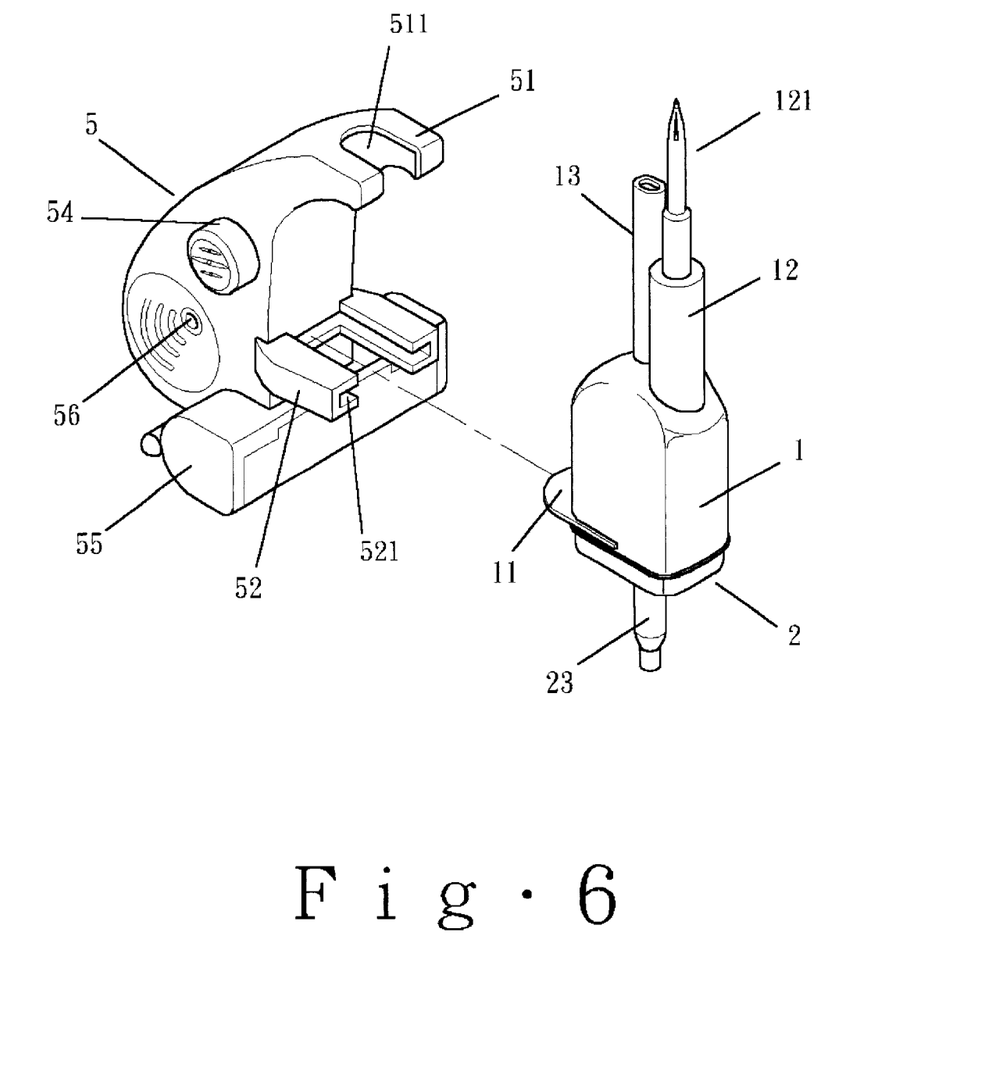
FIG. 6 is a partially exploded view of FIG. 5.
Figure 7:
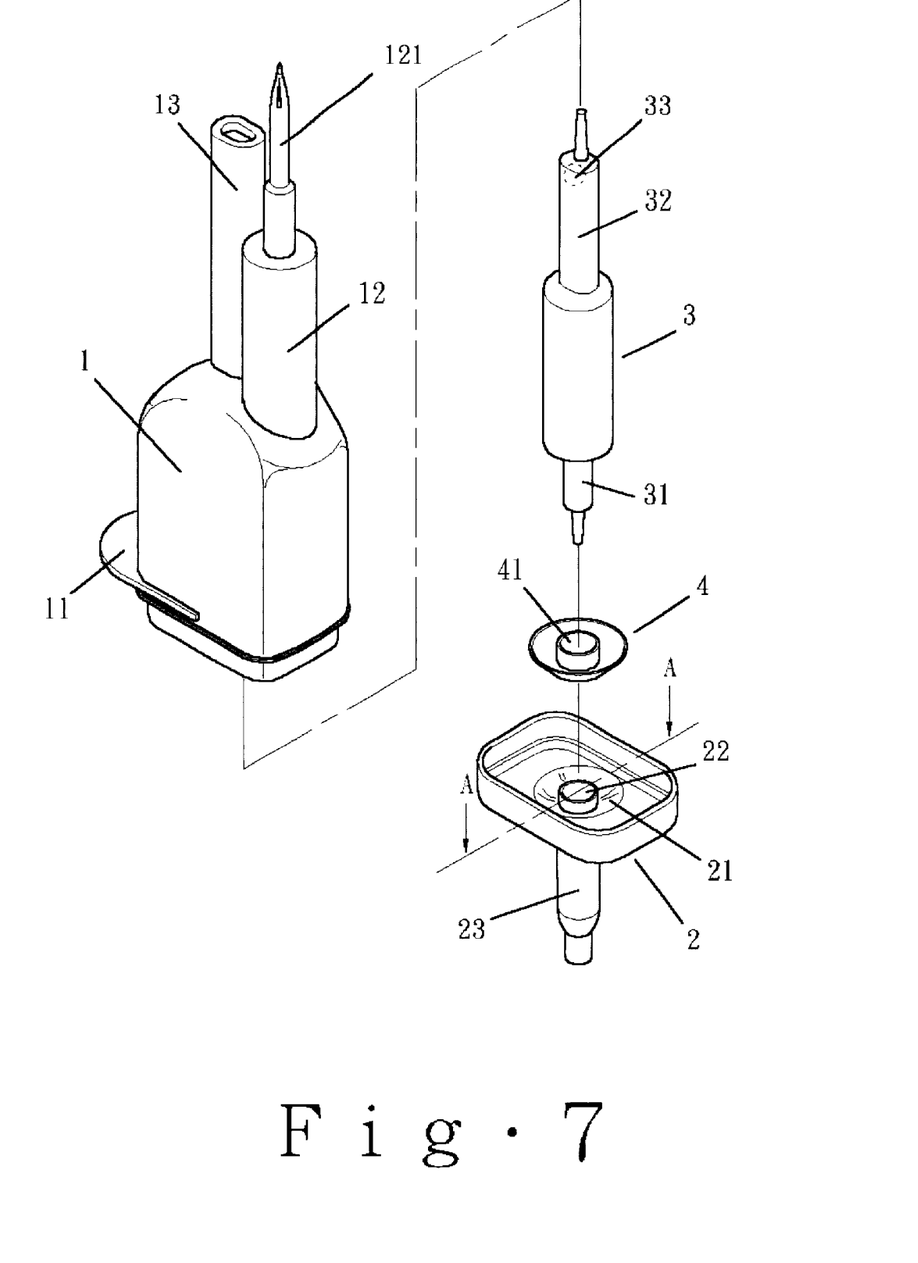
FIG. 7 is a detailedly exploded view of FIG. 5.
Figure 8:
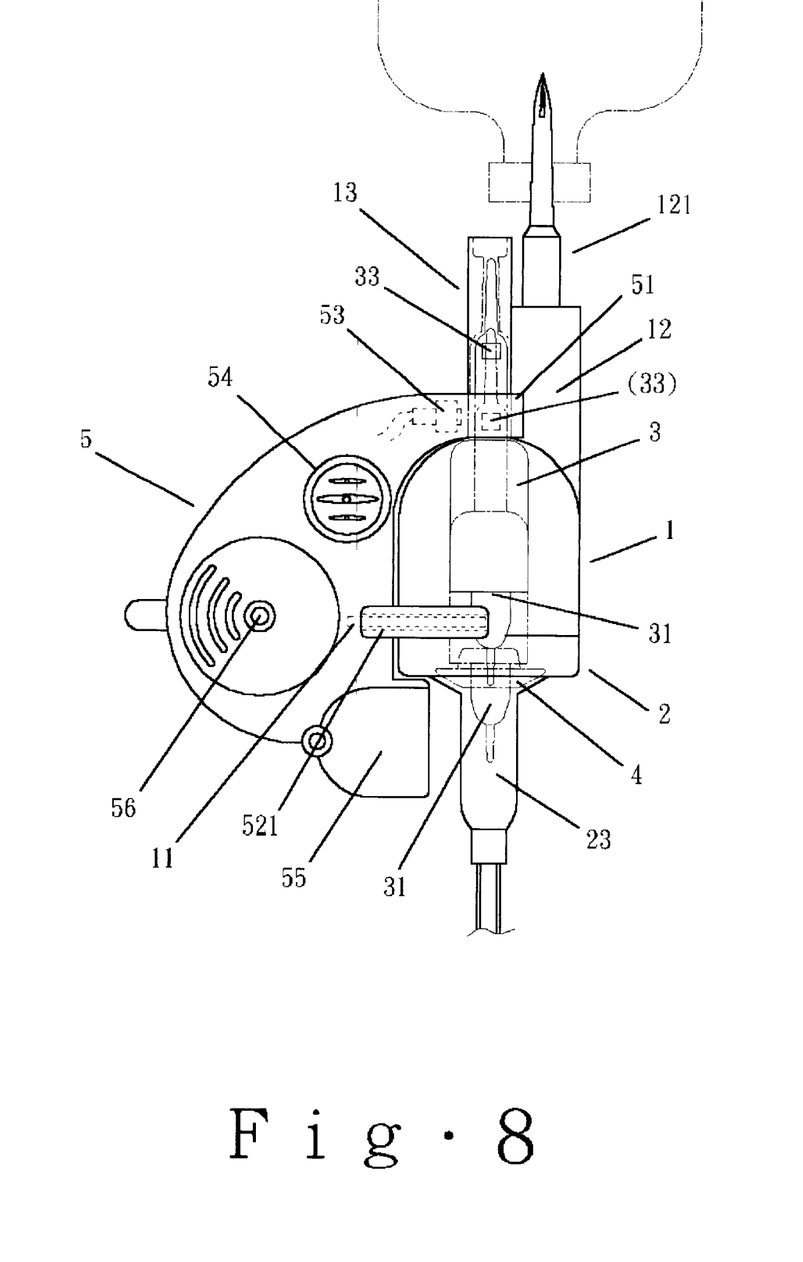
FIG. 8 is a side view of the present invention.

Another prior art, like Taiwan Pat. No. 394026, describes another monitoring device (see FIG. 4) which includes:

an insertion member 20 having an inserting head 21;

an accommodation 30 having a reducing pipe 31 at the bottom thereof for connecting with an injection hose 60 while the insertion member 20 can be stuck to the opening at the top of the accommodation 30; and a stopper 40 with buoyancy disposed inside the accommodation 30.

The accommodation 30 furthermore includes a reducing conic channel 32 at the bottom thereof for connection with a smaller channel 33, and the reducing conic channel 32 has a circular engaging groove 321 at the bottom thereof. When all the infusion solution has flowed out and the solution in the accommodation 30 is reduced to a certain level, the stopper 40 will be engaged into the circular engaging groove 321 of the reducing conic channel 32 of the accommodation 30, thereby forming a sealing state, keeping the air above the remaining solution around the stopper 40 and preventing air from coming into the patient's blood vessel through the injection hose 60. However, the stopper 40 can't exactly seal the circular engaging groove 321 of the accommodation 30 due to the processing precision and the structural restriction, thereby creating clearance therebetween so that the air could enter into the blood vessel.

SUMMARY OF THE INVENTION

It is a primary object according to the present invention to eliminate the aforementioned drawbacks and to provide a nonreturn warning device for an intravenous drip infusion which includes a top member and a bottom member both of which forms an accommodation which has an inlet pipe and an outlet pipe at the top and bottom thereof. The outlet pipe includes a flange around which a recess is provided. A conic valve with a middle hole is arranged onto the flange. A float with a cylindrical stopper is received in the accommodation formed after connection of the top member and the bottom member. The cylindrical stopper falls down against the middle hole of the conic valve when the float sinks with the fluid surface in the accommodation. And the outlet pipe can be choked when all the solution flows out, thereby preventing air from entering into the blood vessel.

It's another object of the present invention to provide a nonreturn warning device for an intravenous drip infusion which has a warning device for clamping the top and bottom members in position. The warning device contains a magnetic reed switch and the float has a magnetic element. When the float sinks with the fluid surface in the accommodation, the magnetic element approaches the magnetic reed switch and a buzzer is activated to give out a warning sound.

It's a further object of the present invention to provide a nonreturn warning device for an intravenous drip infusion in which the warning device is provided with a radio transmitter or a earphone jack in order to facilitate the reception of the warning signal for indicating the end the intravenous drip infusion.

BRIEF DESCRIPTION OF THE DRAWINGS

The drawings disclose illustrative embodiment of the present invention which serves to exemplify the various advantages and objects hereof, and are as follows:

FIG. 2 is a sectional view of FIG. 1 after assembly, showing the dripping state;

FIG. 3 is a sectional view of FIG. 1 after assembly, showing all the infusion solution has flowed out;

DETAILED DESCRIPTION OF THE PREFERRED EMBODIMENT

FIGS. 5 through 9 show the structure of all parts of the present invention. The present invention mainly includes a top member 1, a bottom member 2, a float 3, a conic valve 4 and a warning device 5. The top member 1 is constructed as a housing with an opening at the bottom end thereof and has an insertion piece 11 laterally extending beside the opening at the bottom end of thereof The top member 1 further includes a primary pipe 12 and a secondary pipe 13 both of which extend upward and are parallel to each other. The primary pipe 12 is provided with a pointed bar 121. The bottom member 2 is constructed as a housing with an opening at the top end thereof and has an outlet pipe 23 extending downward at the bottom thereof whose flange 22 projects into the bottom member 2. A recess 21 is formed around the flange 22. The float 3 is a hollow body and is extended with a top cylinder 32 and a cylindrical stopper 31. The top cylinder 32 has a magnetic element 33 in the middle thereof. The conic valve 4 slantly extended, as shown in FIG. 9A, is constructed as a soft body made of rubber while it has a middle hole 41 with a annular groove 42 at the rear side of the middle hole 41 and a rim 421 at the top thereof. The warning device 5 is provided with an upper clamping device 51 and an lower clamping device 52 both of which extends toward the same side. The upper clamping device 51 has a recessed member 511 at the inner side thereof beside which a magnetic reed switch 53 of a buzzer 54 is installed. The lower clamping device 52 includes a clamping slot 521 at two sides thereof, respectively and is (or not) provided with a radio transmitter 55 and/or a headphone jack 56.

In assembly, as shown in FIGS. 5 through 8, the top member 1 and the bottom member 2 is correspondingly connected to each other, thereby creating an accommodation in which the float 3 is arranged in such a was that the top cylinder 32 is inserted into the secondary pipe 13 while the cylindrical stopper 31 of the float 3 is inserted into the outlet pipe 23 of the bottom member 2. Thereafter, the insertion piece 11 of the top member 1 is engaged into the clamping slot 521 so that the insertion piece 11 and the primary pipe 12 are clamped by the lower clamping device 52 and the upper clamping device 51, respectively. Hence, the top member 1, the bottom member 2 and the warning device 5 are connected to one another. In using, the pointed bar 121 is inserted into an I.V. container so that the solution inside flows through the primary pipe 12 into the accommodation between the top member 1 and the bottom member 2 while the float 3 rises with the elevation of the fluid surface. As the I.V. container is empty that the solution won't be supplied through the primary pipe 12 any more and the solution gradually flows from the middle hole 41 of the conic valve 4 through the outlet pipe 23 outwards, the float 3 on the fluid surface inside the accommodation correspondingly descends (see FIGS. 9B and 9C). Meanwhile, the magnetic element 33 in the float 3 also sinks to pass through one side of the magnetic reed switch 53 (see FIG. 8) so that the an electric connection of the buzzer 54 is created by the magnetic reed switch 53 to give out a warning sound, thereby reminding the nurse to replace the old intravenous drip infusion bottle. When the solution in the accommodation between the top member 1 and the bottom member 2 is beneath a certain level (see FIGS. 9C and 9D), the buoyancy is not enough to raise the float 3. At this time, the cylindrical stopper 31 of the float 3 blocks the middle hole 41 of the conic valve 4. Besides, the inwardly grooved member 310 around the cylindrical stopper 31 lies against the top rim 421 of the middle hole 41 of the conic valve 4 in such a way that only a tiny amount of solution can flow through the clearance between the cylindrical stopper 31 and the middle hole 41. Accordingly, not only the time of the solution inside the accommodation flowing through the outlet pipe 23 can be prolonged, but also the solution can stay inside the solution channel between the outlet pipe 23 and the human body for a longer time. In addition, the tip of the hypodermic needle pierced into the tissue can be humidified for preventing the blood platelet from coagulation. Which makes the tip of the needle to be choked. With the fluid level lower and lower, the middle hole 41 is sealed by the cylindrical stopper 31 more and more tightly until almost a vacuum suction state is reached.

Again, referring to FIG. 7, the top cylinder 32 of the float 3 is constructed in an form with two parallel sides and the other two arched sides or in an oval form. When the float rises and sinks within the accommodation, the magnetic element 33 in the middle section thereof can be maintained in a fixed passage so as to correspond to the magnetic reed switch 53 of the warning device 5

Figure 9A:
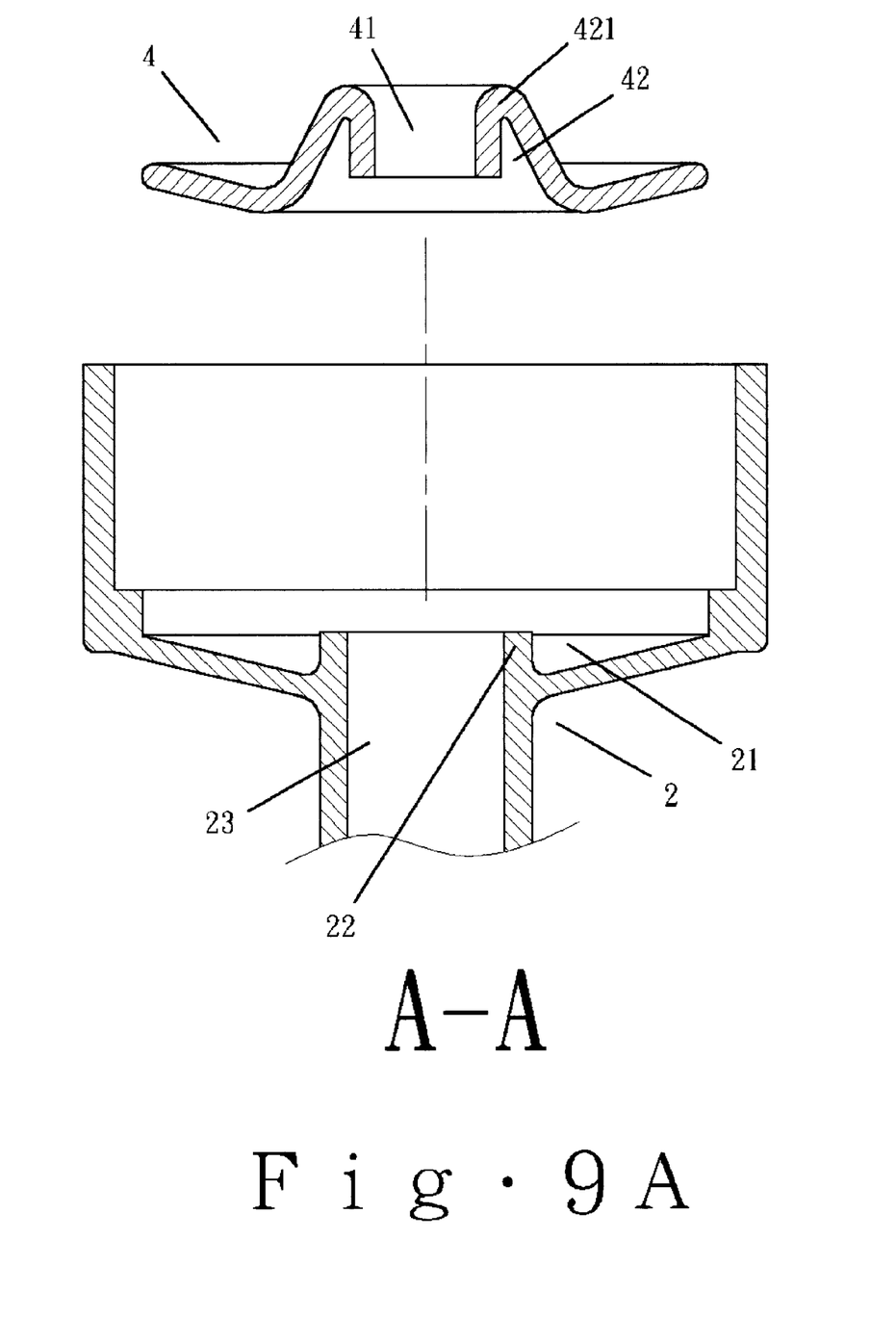
FIG. 9A is a cross-section taken along the line of A—A of FIG. 7, showing the conic valve and the recess.
Figure 9B:
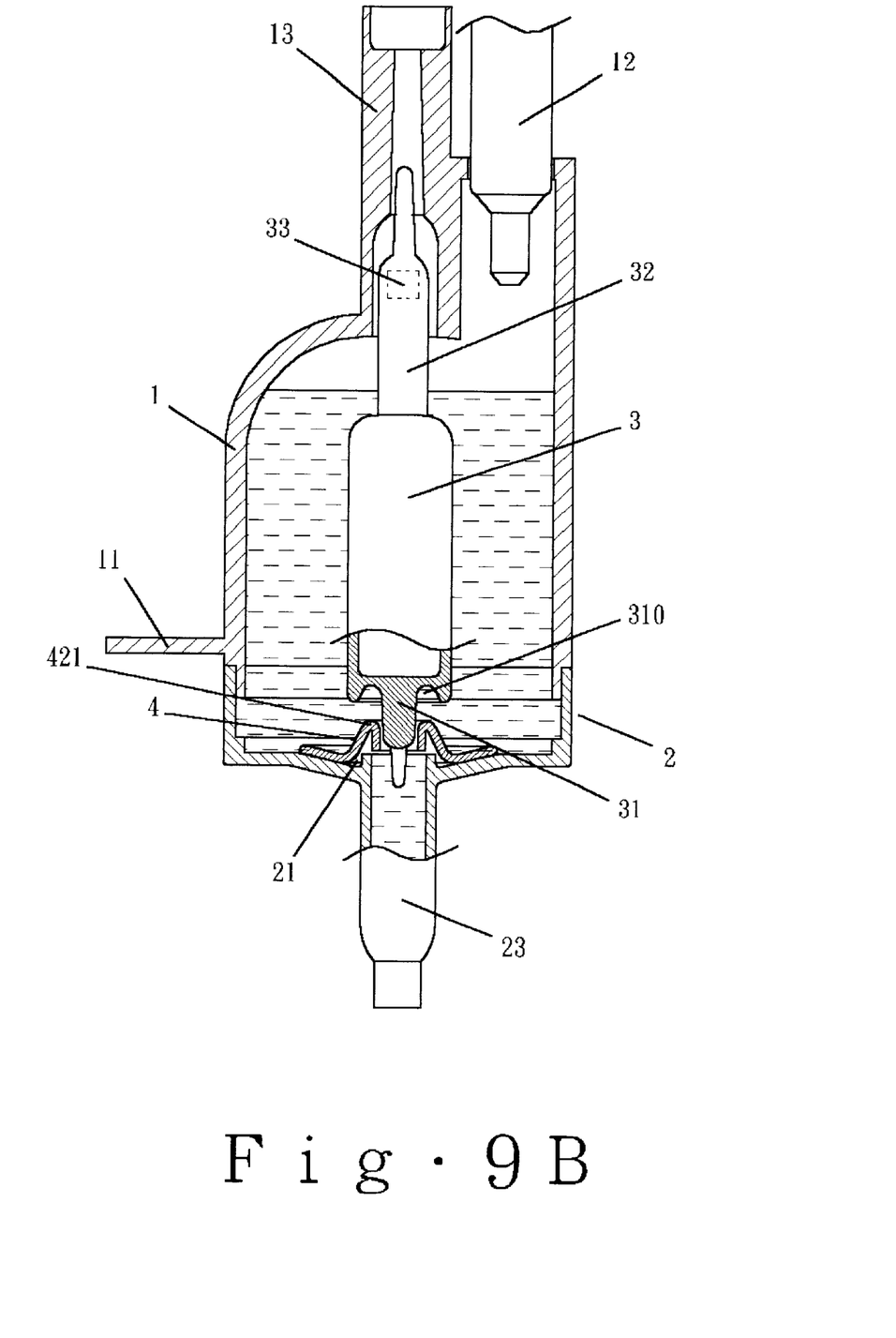
FIG. 9B is a first sectional view of the present invention, showing the action between the float and the conic valve.
Figure 9C:
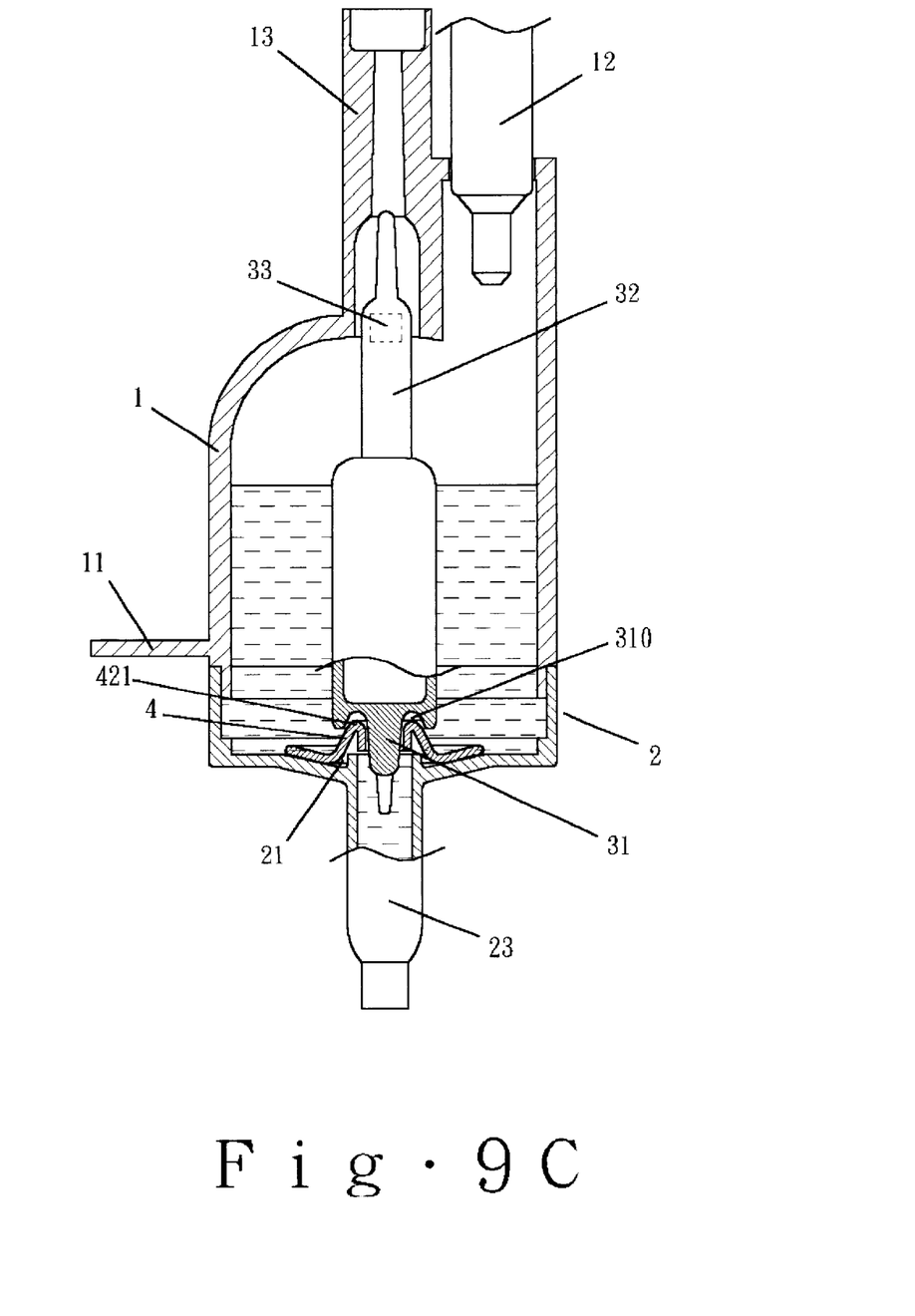
FIG. 9C is a second sectional view of the present invention, showing the action between the float and the conic valve.
Figure 9D:
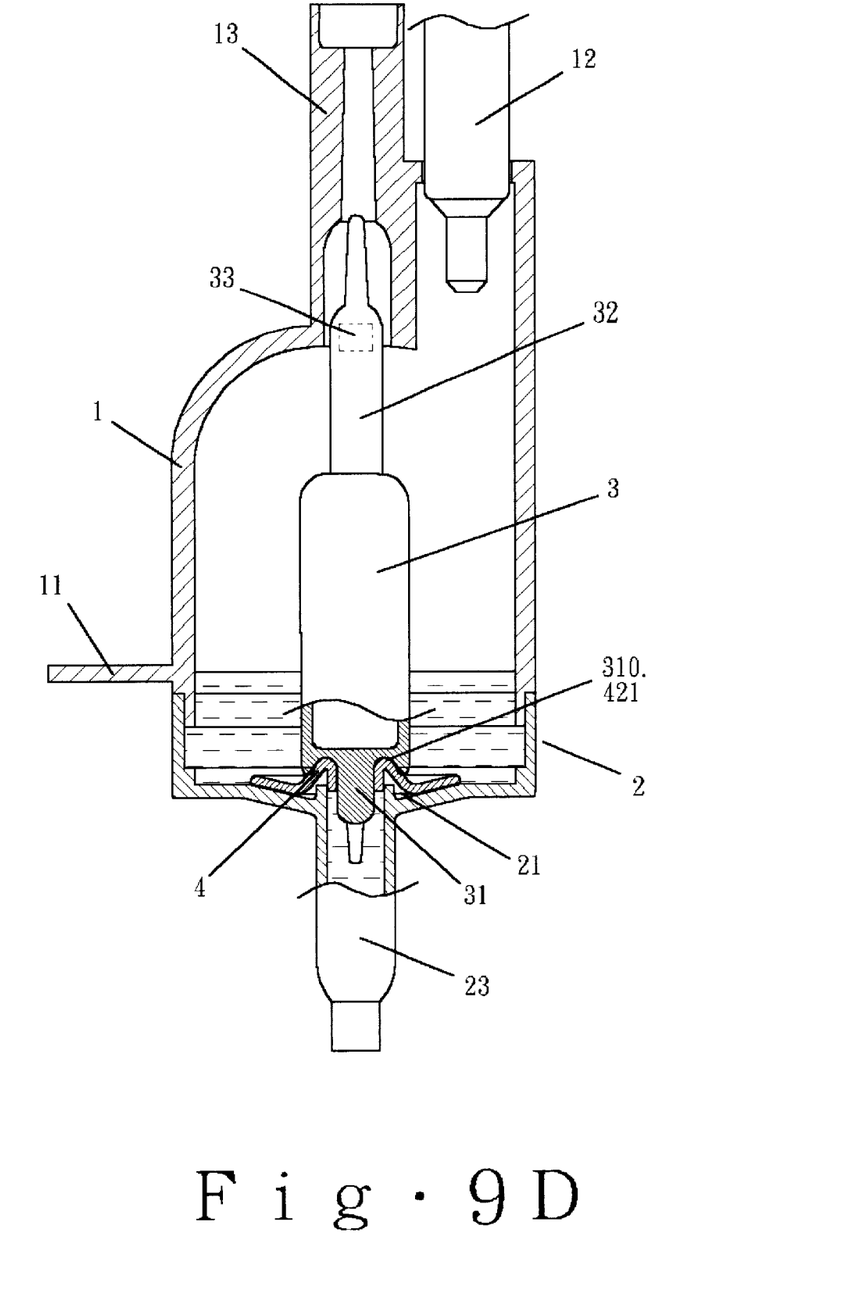
FIG. 9D is a third sectional view of the present invention, showing the action between the float and the conic valve.
Figure 9E:
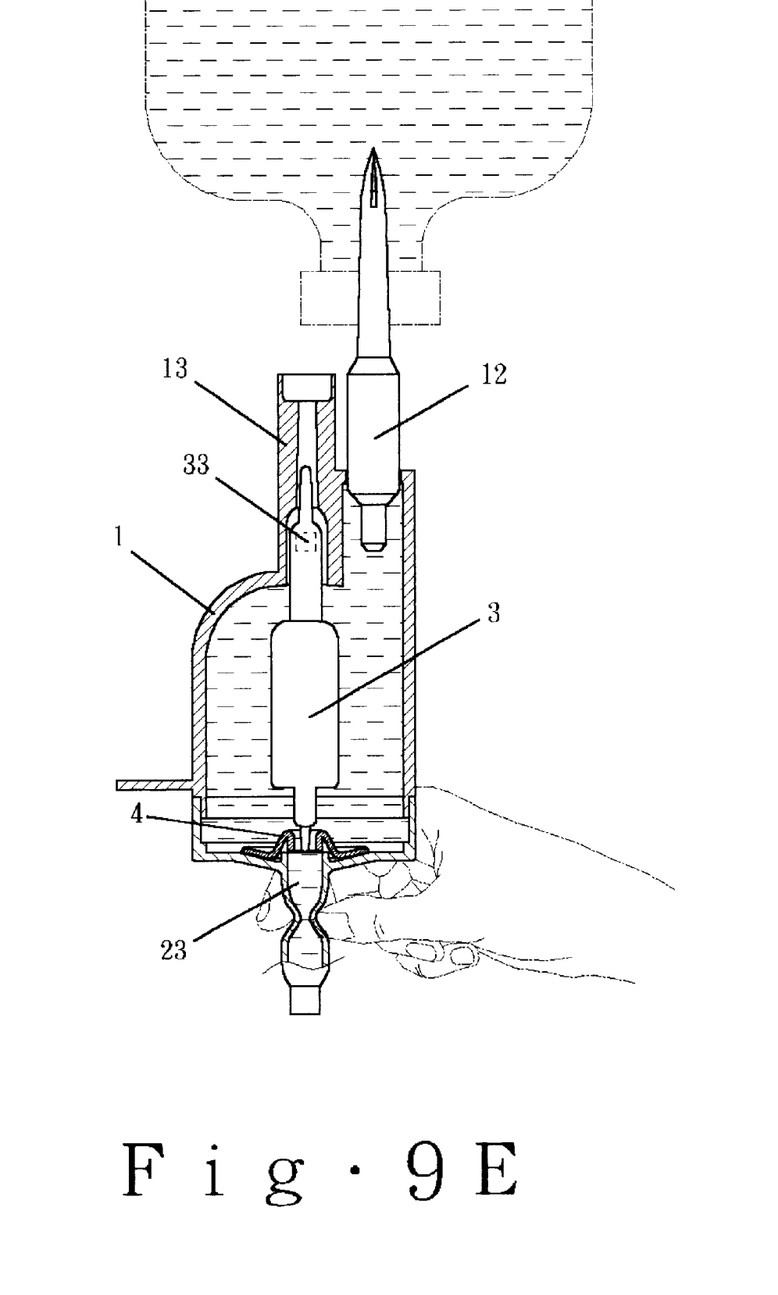
FIG. 9E is a sectional view of the present invention, showing the float rises in pressing the out let pipe.

Furthermore, referring to FIG. 9E, when it's required to replace an I.V. container, the middle hole 41 of the conic valve 4 are tightly sealed by the cylindrical stopper 31 of the float 3 in a vacuum suction state while the float 3 can't automatically float upward as welt after replacement of the I.V. container. Consequently, the float 3 can be pushed upward by a returning impulse of infusion solution created by pinching the outlet pipe 23 with fingers.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A nonreturn warning device for an intravenous drip infusion at least comprising:

a top member having an opening at the bottom end thereof, a primary pipe and a secondary pipe both of which extend upward and are parallel to each other, said primary pipe being provided with a pointed bar;

a bottom member having an opening at the top end thereof, an accommodation being formed by means that said top member and said bottom member are connected to each other, an outlet pipe extending downward at the bottom thereof, a flange projected into said bottom member and a recess being formed around said flange;

a float constructed as a hollow cylinder and arranged in said accommodation between said top member and said bottom member, said float having a top cylinder extending into said secondary pipe and a cylindrical stopper extending into said outlet pipe; and a conic valve constructed as a soft body made of rubber while said conic valve has a middle hole for passage of the cylindrical stopper, with an annular groove at the rear side of the middle hole and a rim at the top thereof, said annular groove being engaged with said flange.

2. The nonreturn warning device for an intravenous drip infusion as recited in claim 1, wherein a warning device is connected to said top member, and a magnetic reed switch in connection with a buzzer is installed in said warning device, and said float includes a magnetic element in the middle of said top cylinder, and as said float correspondingly sinks with the fluid surface, said magnetic element passes through one side of said magnetic reed switch to activate said magnetic reed switch while an electric connection of said buzzer is created by said magnetic reed switch to give out a warning sound.

3. The nonreturn warning device for an intravenous drip infusion as recited in claim 2, wherein said warning device includes an upper clamping device having a recessed member at the inner side thereof into which said primary pipe of said top member is engaged.

4. The nonreturn warning device for an intravenous drip infusion as recited in claim 2, wherein said warning device includes an lower clamping device having a clamping slot at two sides thereof, respectively, and said top member has an insertion piece laterally extending near the bottom end of thereof which is engaged into said clamping slots in place.

5. The nonreturn warning device for an intravenous drip infusion as recited in claim 1 or 2, wherein said warning device includes a radio transmitter at a proper place thereof.

6. The nonreturn warning device for an intravenous drip infusion as recited in claim 1 or 2, wherein said warning device doesn't include a radio transmitter.

7. The nonreturn warning device for an intravenous drip infusion as recited in claim 1 or 2, wherein said warning device includes a headphone jack.

* * * * *